United States Patent
Schmidt et al.

(10) Patent No.: US 7,141,701 B1
(45) Date of Patent: *Nov. 28, 2006

(54) DECOMPOSITION OF CUMENE HYDROPEROXIDE

(75) Inventors: Robert J. Schmidt, Barrington, IL (US); Russell C. Schulz, Glen Ellyn, IL (US); Patrick J. Bullen, Elmhurst, IL (US); Constante P. Tagamolila, Arlington Heights, IL (US); Steven P. Lankton, Wheeling, IL (US); Gary A. Peterson, Naperville, IL (US); Michael E. Fettis, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/207,951

(22) Filed: Aug. 19, 2005

(51) Int. Cl.
*C07C 45/00* (2006.01)
*C07C 37/08* (2006.01)
*C07C 15/40* (2006.01)

(52) U.S. Cl. .................. 568/385; 568/411; 568/798; 585/435

(58) Field of Classification Search .................. None
See application file for complete search history.

(56) References Cited

U.S. PATENT DOCUMENTS

| 4,358,618 A | 11/1982 | Sifniades et al. ........... 568/385 |
| 6,201,157 B1 | 3/2001 | Keenan ...................... 568/798 |
| 6,307,112 B1 | 10/2001 | Weber et al. ............... 568/798 |

*Primary Examiner*—Sikarl A. Witherspoon
(74) *Attorney, Agent, or Firm*—John G. Tolomei; James C. Paschall; John G. Cutts, Jr.

(57) ABSTRACT

A process for decomposing a cumene oxidation product mixture containing cumene hydroperoxide (CHP) and dimethylphenolcarbinol (DMPC) to produce phenol and acetone.

25 Claims, 2 Drawing Sheets

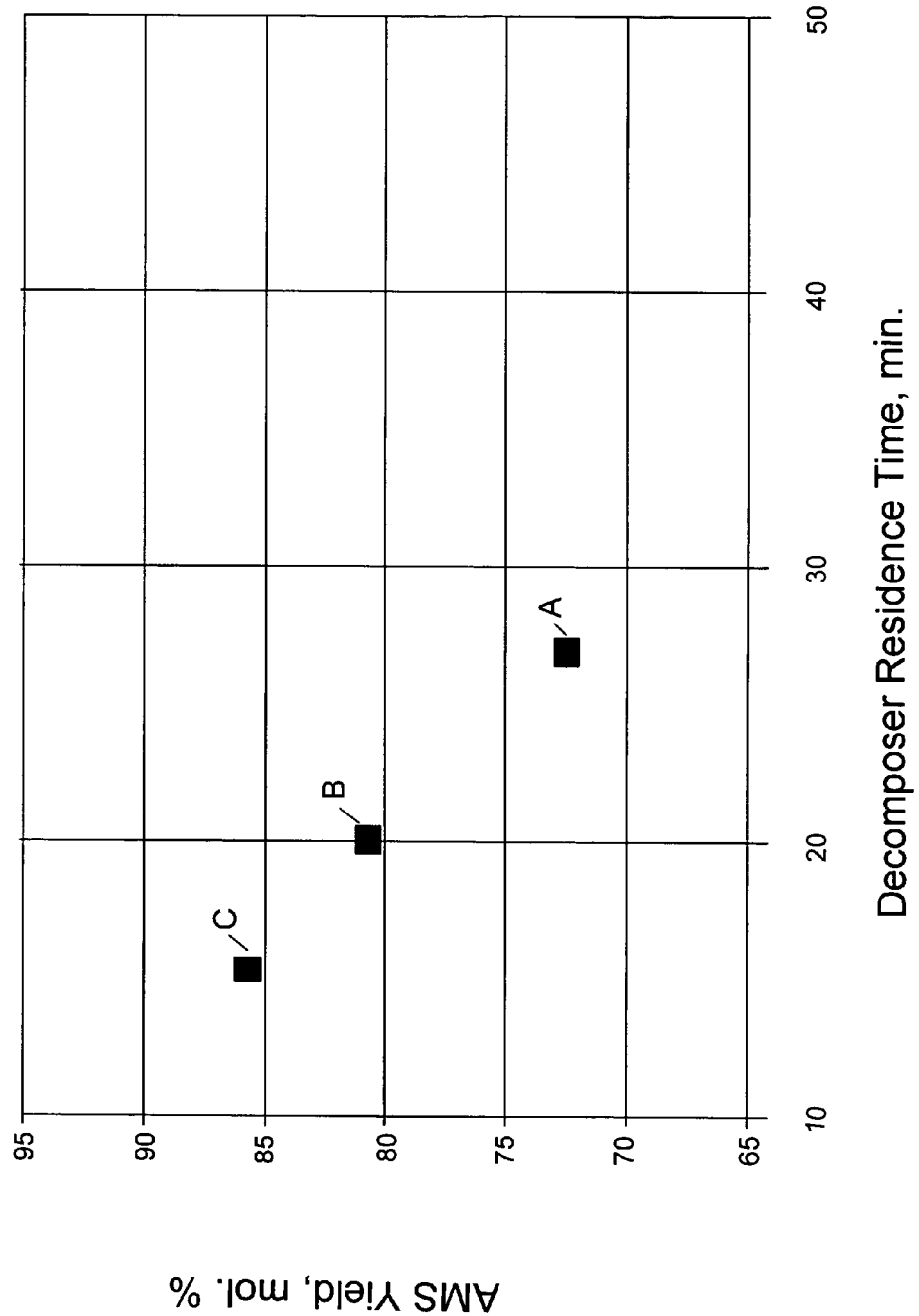

DECOMPOSITION OF CUMENE HYDROPEROXIDE

BACKGROUND OF THE INVENTION

Phenol is manufactured via air oxidation of cumene to cumene hydroperoxide (CHP), followed by acid-catalyzed cleavage of the latter to phenol and acetone, and is known as CHP decomposition. CHP decomposition is a very exothermic reaction which is normally carried out on a commercial scale in continuous stirred or back-mixed reactors. In such reactors only a small fraction of CHP is unreacted at any given time and the reaction medium consists essentially of the products of decomposition of CHP, i.e., phenol and acetone, plus any solvent (e.g., cumene) and other materials added with CHP to the reactor. During cumene oxidation small amounts of dimethyl phenyl carbinol (DMPC) and acetophenone are also formed. In the presence of acid catalyst, DMPC dehydrates to alphamethylstyrene (AMS), a useful by-product. Very high yields of AMS can be obtained from pure DMPC, e.g., 98% yield upon dehydration over acidic silica at 300° C. In the presence of phenol, however, and more specifically in a phenol/acetone/cumene mixture which is a solvent in the decomposition of CHP/DMPC mixtures, the ultimate AMS yield is normally about 50–60 mol % of the DMPC. Main by-products are AMS dimers and cumylphenol which have no commercial value. Formation of cumylphenol also reduces the phenol yield.

Although phenol and acetone have been produced by the decomposition of the cumene oxidation product for decades, there is a continuing incentive to produce at a lower cost and with reduced by-product formation.

INFORMATION DISCLOSURE

U.S. Pat. No. 4,358,618 (Sifniades et al.) discloses a multi-step process for the production of acetone and phenol by the decomposition of cumene hydroperoxide.

U.S. Pat. No. 6,201,157 B1 (Keenan) discloses a process for the decomposition of cumene hydroperoxide using an acid catalyst and neutralizing the acid catalyst after the completion of the decomposition by the addition of an amine.

U.S. Pat. No. 6,307,112 (Weber et al.) discloses a process for cleaving cumene hydroperoxide wherein the mass flow ratio of a recycled partial product stream to the cumene hydroperoxide-containing feed stream sent to the cleavage reactor is less than 10. The patent discloses the use of vertical tube bundle heat exchangers.

BRIEF SUMMARY OF THE INVENTION

The present invention is a process for the decomposition of a cumene oxidation product to produce phenol and acetone with reduced by-product formation by introducing the cumene oxidation product mixture into a vessel maintained at specified operating conditions before being introduced into a circulating loop comprising cumene hydroperoxide, an acid catalyst, phenol and acid while removing the exothermic heat of reaction from the circulating loop and withdrawing a reacted stream comprising a cumene hydroperoxide concentration from about 0.5 to about 5 weight percent from the circulating loop. In one embodiment of the present invention, the heat removal from the circulating loop is conducted by the use of vertically arranged heat exchanger(s). In another embodiment, acetone is recycled to the circulating loop.

BRIEF DESCRIPTION OF THE DRAWINGS

FIG. 2 is graph showing alphamethylstyrene (AMS) yield as a function of a decomposer residence time.

DETAILED DESCRIPTION OF THE INVENTION

Figure 1:
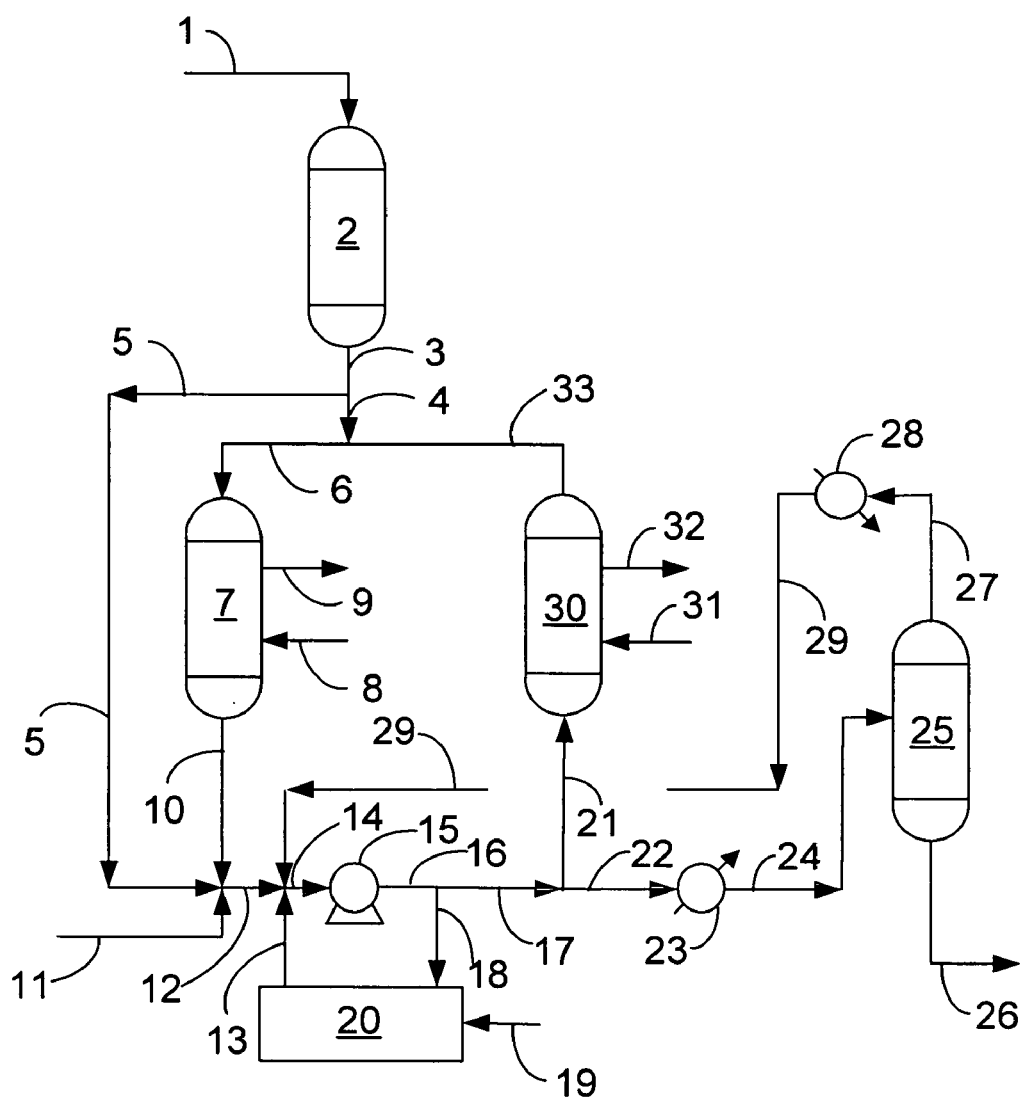
FIG. 1 is a schematic flow diagram of a preferred embodiment of the present invention for decomposing a cumene oxidation product mixture containing cumene hydroperoxide (CHP) and dimethylphenolcarbinol (DMPC) to produce phenol and acetone.

It has been discovered that when a cumene oxidation product mixture containing cumene hydroperoxide (CHP) and DMPC is decomposed to produce phenol, acetone and alpha-methyl styrene, by passing the cumene oxidation product mixture into a vessel having a liquid hourly space velocity (LHSV) from about 10 $hr^{-1}$ to about 30 $hr^{-1}$ and then passing the cumene oxidation product mixture into a circulating loop comprising cumene hydroperoxide, an acid catalyst, phenol and acetone thereby producing an exothermic heat of reaction, an improved yield of alpha-methyl styrene is realized. The cumene oxidation product mixture is the result of cumene oxidation with oxygen and preferably comprises a cumene hydroperoxide concentration from about 60 to about 95 weight percent. The ratio of the flow rate of the cumene oxidation product mixture to the flow rate of the circulating loop is preferably from about 1:10 to about 1:100. In accordance with the present invention, a suitable and preferred acid catalyst is sulfuric acid.

The initial primary vessel or predecomposer vessel which is operated at a liquid hourly space velocity from about 10 $hr^{-1}$ to about 30 $hr^{-1}$ is preferably operated at a temperature from about 50° C. (122° F.) to about 80° C. (176° F.) and a pressure from about 115 kPa (2 psig) to about 618 kPa (75 psig). This vessel serves as a metering vessel. The resulting effluent from the primary or metering vessel is introduced into a circulating loop preferably maintained at a temperature from about 50° C. (122° F.) to about 80° C. (176° F.) and a pressure sufficient to maintain a liquid phase. The metering vessel is used to control the flow of CHP to the circulating CHP decomposition loop. The decomposition of the cumene hydroperoxide is highly exothermic and therefore heat must be removed from the circulating loop to maintain the preferred operating temperature. In accordance with the present invention, the circulating loop is passed through at least one indirect heat exchanger to maintain the desired decomposition temperature. The heat exchanger(s) is preferably oriented in a generally vertical position operating in a counter-current mode which enables the maintenance of an evenly and consistently controlled heat removal, low residence time and optimal placement which minimizes the overall area required for the plant. By "generally vertical position" it is meant that the principal axis of a heat exchanger is situated in a generally vertical location or position. Any suitable heat exchanger may be utilized for the present invention including a shell and tube heat exchanger or a U-tube heat exchanger, for example. The preferred vertical orientation of the heat exchangers enables the use of short, compact, low-volume manifolding and piping to permit a low decomposition residence time in the circulation loop which maximizes the production of desired product while minimizing the production of undesirable high molecular weight by-products.

A portion of the flowing liquid in the circulating loop, preferably containing from about 0.5 to about 5 weight percent cumene hydroperoxide, is removed from the circulating loop. Varying amounts of dicumyl peroxide (DCP) are also present in the removed portion and is preferably decomposed in a dehydrator to mainly yield phenol, acetone and alpha-methylstyrene (AMS) by increasing the temperature in the range from about 100° C. (212° F.) to about 170° C. (338° F.). The same higher temperature conditions that favor formation of AMS from DCP also favor the dehydration of dimethyl phenyl carbinol (DMPC) to AMS. It is therefore convenient to transform both the DMPC and the DCP present in the reaction mixture resulting from the acid catalyzed decomposition of CHP by simply heating that mixture to 100° C. (212° F.)–170° C. (338° F.) for a limited period of time in a plug-flow reactor referred to as a dehydrator. The dehydrator generally is composed of a heat exchanger in which the reaction mixture is brought up to the desired temperature, in series with a pipe or baffled tank, in which the reaction is completed. The latter part of the reactor is essentially isothermal. The yield of AMS formed in the reaction increases with time as DCP and the residual DMPC decompose, until it reaches a maximum and then decreases as AMS reacts further to form AMS dimers and cumylphenol. The optimum reaction time depends on the temperature and the concentrations of acid catalyst and water present in the mixture. Generally, shorter times are required at higher temperatures and in the presence of higher concentrations of acid and lower concentrations of water.

In accordance with one embodiment, after the decomposition reaction of the CHP is completed in the dehydrator, the resulting effluent therefrom is introduced into a flash drum to vaporize at least a portion of the acetone which is subsequently condensed and introduced into the circulating loop. The acetone is preferably recycled and introduced into the circulating loop wherein the weight ratio of the acetone recycle to the cumene oxidation product mixture is in the range from about 0.1:1 to about 2:1. A resulting liquid stream comprising phenol and acetone is removed from the flash drum and fractionated to further separate the products.

DETAILED DESCRIPTION OF THE DRAWINGS

In FIG. 1, a cumene oxidation product stream containing CHP is introduced into the process via line 1 and enters metering vessel 2. A resulting stream containing cumene oxidation product is removed from metering vessel 2 via line 3 and a portion thereof is transported via line 4 and joins a flowing circulating loop carried in line 33 and the resulting admixture is transported via line 6 and introduced into vertical heat exchanger 7. A cooling medium is provided via line 8 and is introduced into vertical heat exchanger 7 and a resulting heated medium is removed via line 9 and recovered. The cooling medium may be recirculated after cooling, if desired. A cooled process stream is removed from vertical heat exchanger 7 via line 10 and is admixed with another portion of the cumene oxidation product stream provided via lines 3 and 5, and a make-up acetone stream provided via line 11. The resulting mixture is transported via line 12 and is admixed with an acetone recycle stream provided via line 29 and the resulting admixture is carried via line 14 and introduced into pump 15. A resulting stream is transported from pump 15 via lines 16 and 17. At least a portion of the flowing stream in line 17 is carried via line 21 and introduced into vertical heat exchanger 30. A cooling medium is provided via line 31 and introduced into vertical heat exchanger 30 and a resulting heated medium is removed from vertical heat exchanger 30 via line 32. A cooled flowing stream is removed from vertical heat exchanger 30 via line 33 and is admixed with cumene oxidation product as hereinabove described. A portion of the flowing stream in line 15 is transported via line 18 and introduced into calorimeter 20 which is used to monitor and control the operating conditions for the decomposition of the CHP. A sulfuric acid stream is carried via line 19 and introduced into calorimeter 20. The resulting admixture from calorimeter 20 is introduced into line 14 via line 13. Another portion of the flowing stream in line 17 is carried via line 22 and introduced into heat exchanger 23 to be heated. A resulting heated stream is removed from heat exchanger 23 via line 24 and introduced into flash drum 25. A stream rich in acetone is removed from flash drum 25 via line 27 and introduced into heat exchanger 28. A resulting cooled stream is removed from heat exchanger 28 via line 29 and introduced into line 14. A stream containing acetone and phenol is removed from flash drum 25 via line 26 and recovered.

In FIG. 2, three data points, (A, B and C) from the Illustrative Embodiment are plotted in a graph showing alphamethylstyrene (AMS) yield as a function of a decomposer residence time.

Illustrative Embodiment

A cumene oxidation product mixture containing 79 weight percent cumene hydroperoxide at a rate of 41.8 m³/hr is passed through a metering vessel maintained at a temperature of about 60° C. (140° F.) and at a liquid hourly space velocity of 30 hr⁻¹ with an average residence time of 26 minutes. The resulting effluent in an amount of 41.8 m³/hr from the metering vessel is introduced into a circulating decomposer loop having a volume of 18.1 m³. The circulating decomposer loop is operated at a residence time of 26 minutes, a sulfuric acid level of 54 wppm and temperature of 60° C. to produce a decomposer product containing a CHP concentration of 0.63 weight percent. The resulting decomposer effluent is passed through a dehydrator operated at a temperature of 120° C. The resulting AMS yield is 72.7 mol % and the cumene/phenol yield ratio is 1.322. This run is in accordance with the present invention. The results are summarized and presented in Table 1 as Run A. The AMS yield result is plotted in FIG. 2 and is identified as point "A".

A cumene oxidation product mixture containing an 83 weight percent cumene hydroperoxide at a rate of 39.8 m³/hr is passed through a metering vessel maintained at a temperature of about 60° C. (140° F.) and at a liquid hourly space velocity of 30 hr⁻¹ with an average residence time of 20 minutes. The resulting effluent in an amount of 39.8 m³/hr from the vessel is introduced into circulating decomposer loop having a volume of 13.3 m³. This lower volume in the circulating decomposer loop is made possible by the use of two vertically oriented heat exchangers. The circulating decomposer loop is operated at a residence time of 20 minutes, a sulfuric acid level of 40 wppm and a temperature of 60° C. to produce a decomposer product containing a CHP concentration of 1.5 weight percent. The resulting decomposer effluent is passed through a dehydrator operated at a temperature of 135° C. The resulting AMS yield is 80.6 mol % and the cumene/phenol yield ratio is 1.311. This run is in accordance with the present invention. The results are summarized and presented in Table 1 as Run A. The AMS yield result is plotted in FIG. 2 and is identified as point "B".

A cumene oxidation product mixture containing an 88.5 weight percent cumene hydroperoxide at a rate of 26 m³/hr is passed through a metering vessel maintained at temperature of about 75° C. (167° F.) and at a liquid hourly space velocity of 30 hr$^{-1}$ with an average residence time of 15 minutes. The resulting effluent at a rate of 26 m$^3$/hr from the vessel is introduced into a circulating decomposer loop having a volume of 12.5 m$^3$. Two vertically oriented heat exchangers are used in this run along with an acetone recycle in an amount of 8.6 m$^3$/hr. the circulating decomposer loop is operated at a residence time of 15 minutes, a sulfuric acid level of 6 wppm and a temperature of 75° C. to produce a decomposer product containing a CHP concentration of 3.0 weight percent. The resulting decomposer effluent is passed through a dehydrator operated at a temperature of 135° C. The resulting AMS yield is 85.5 mol % and the cumene/phenol yield ratio is 1.290. Thus the yield ratio has improved using the process of this invention to a level where it is now very close to the theoretical limit for this type of chemistry of 1.277. This run is in accordance with the present invention. The results are summarized and presented in Table 1 as Run C. The AMS yield result is plotted in FIG. 2 and is identified as point "C".

TABLE 1

Operation Summary

| RUN | A | B | C |
| --- | --- | --- | --- |
| CLIP Concentration, wt % | 79 | 83 | 88.5 |
| Predecomposer vessel, LHSV | 30 | 30 | 30 |
| Decomposer feed rate, m$^3$/hr. | 41.8 | 39.8 | 2.6 |
| Decomposer volume, m$^3$ | 18.1 | 13.3 | 12.5 |
| Decomposer residence time, min. | 26 | 20 | 15 |
| Decomposer acid level, wppm | 54 | 40 | 6 |
| Decomposer temperature, ° C. | 60 | 60 | 75 |
| Decomposer product CLIP level, wt % | 0.63 | 1.5 | 3.0 |
| Dehydrator temperature, ° C. | 120 | 135 | 135 |
| Cumene Feed/phenol yield ratio, wt/wt | 1.322 | 1.311 | 1.290 |
| AMS Yield, mol % | 72.7 | 80.6 | 85.5 |
| Cumene feed/phenol yield ratio, mol/mol | 0.966 | 0.974 | 0.989 |

The foregoing description, drawings and illustrative embodiment clearly illustrate the advantages encompassed by the process of the present invention and the benefits to be afforded with the use thereof.

What is claimed is:

1. A process for decomposing a cumene oxidation product mixture containing cumene hydroperoxide (CHP) and dimethylphenylcarbinol (DMPC) to produce phenol, acetone, and alpha-methyl styrene (AMS) with reduced by-product formation which comprises:
    (a) introducing the cumene oxidation product mixture into a metering vessel operated at a temperature from about 50° C. (122° F.) to about 80° C. (176° F.) and a pressure from about 115 kPa (2 psig) to about 618 kPa (75 psig);
    (b) flowing the cumene oxidation product mixture from step (a) into a circulating loop comprising cumene hydroperoxide, an acid catalyst, phenol and acetone at a temperature from about 50° C. (122° F.) to about 80° C. (176° F.) while producing an exothermic heat of reaction;
    (c) removing the exothermic heat of reaction from the circulating loop; and
    (d) withdrawing a reacted stream comprising a cumene hydroperoxide concentration from about 0.5 to about 5 weight percent from the circulating loop.

2. The process of claim 1 wherein the cumene oxidation product mixture comprises a cumene hydroperoxide concentration from about 60 to about 95 weight percent.

3. The process of claim 1 wherein the ratio of the flow rate of cumene oxidation product mixture to the flow rate of the circulating loop is from about 1:10 to about 1:100.

4. The process of claim 1 wherein the acid catalyst is sulfuric acid.

5. The process of claim 1 wherein step (c) is conducted with one or more indirect heat-exchangers.

6. The process of claim 5 wherein the indirect heat-exchangers are essentially vertical.

7. A process for decomposing a cumene oxidation product mixture containing cumene hydroperoxide (CHP) and dimethylphenylcarbinol (DMPC) to produce phenol, acetone and alpha-methyl styrene (AMS) with reduced by-product formation which comprises the steps:
    (a) introducing the cumene oxidation product mixture into a metering vessel having a liquid hourly space velocity of from about 10 hr$^{-1}$ to about 30 hr$^{-1}$ and operated at a temperature from about 50° C. (122° F.) to about 80° C. (176° F.) and a pressure from about 115 kPa (2 psig) to about 618 kpa (75 psig);
    (b) flowing the cumene oxidation product mixture from step (a) into a circulating loop comprising cumene hydroperoxide, an acid catalyst, phenol and acetone at a temperature from about 50° C. (122° F.) to about 80° C. (176° F.) while producing an exothermic heat of reaction;
    (c) removing the exothermic heat of reaction from the circulating loop; and
    (d) withdrawing a reacted stream comprising a cumene hydroperoxide concentration from about 0.5 to about 5 weight percent from the circulating loop.

8. The process of claim 7 wherein the cumene oxidation product mixture comprises a cumene hydroperoxide concentration from about 60 to about 95 weight percent.

9. The process of claim 7 wherein the ratio of the flow rate of cumene oxidation product mixture to the flow rate of the circulating loop is from about 1:10 to about 1:100.

10. The process of claim 7 wherein the acid catalyst is sulfuric acid.

11. The process of claim 7 wherein step (c) is conducted with one or more indirect heat-exchangers.

12. The process of claim 11 wherein the indirect heat-exchangers are essentially vertical.

13. A process for decomposing a cumene oxidation product mixture containing cumene hydroperoxide (CHP) and dimethylphenylcarbinol (DMPC) to produce phenol, acetone and alpha-methyl styrene (AMS) with reduced by-product formation which comprises the steps:
    (a) introducing the cumene oxidation product mixture into a metering vessel operated at a temperature from about 50° C. (122° F.) to about 80° C. (176° F.) and a pressure from about 115 kPa (2 psig) to about 618 kPa (75 psig);
    (b) flowing the cumene oxidation product mixture from step (a) into a circulating loop comprising cumene hydroperoxide, an acid catalyst, phenol and acetone at a temperature from about 50° C. (122° F.) to about 80° C. (176° F.) while producing an exothermic heat of reaction;
    (c) removing the exothermic heat of reaction from the circulating loop with one or more vertically oriented heat-exchangers; and
    (d) withdrawing a reacted stream comprising a cumene hydroperoxide concentration from about 0.5 to about 5 weight percent from the circulating loop.

14. The process of claim 13 wherein the cumene oxidation product mixture comprises a cumene hydroperoxide concentration from about 60 to about 95 weight percent.

15. The process of claim 13 wherein the ratio of the flow rate of cumene oxidation product mixture to the flow rate of the circulating loop is from about 1:10 to about 1:100.

16. The process of claim 13 wherein the acid catalyst is sulfuric acid.

17. The process of claim 13 wherein the heat-exchangers are shell and tube heat exchangers.

18. The process of claim 13 wherein the vessel in step (a) is operated with a liquid hourly space velocity from about 10 $hr^{-1}$ to about 30 $hr^{-1}$.

19. A process for decomposing a cumene oxidation product mixture containing cumene hydroperoxide (CHP) and dimethylphenylcarbinol (DMPC) to produce phenol, acetone and alpha-methyl styrene (AMS) with reduced by-product formation which comprises the steps:
- (a) introducing the cumene oxidation product mixture into a metering vessel operated at a temperature from about 50° C. (122° F.) to about 80° C. (176° F.) and a pressure from about 115 kPa (2 psig) to about 618 kPa (75 psig);
- (b) flowing the cumene oxidation product mixture from step (a) into a circulating loop comprising cumene hydroperoxide, an acid catalyst, phenol and acetone at a temperature from about 50° C. (122° F.) to about 80° C. (176° F.) while producing an exothermic heat of reaction;
- (c) removing the exothermic heat of reaction from the circulating loop;
- (d) withdrawing a reacted stream comprising acetone and a cumene hydroperoxide concentration from about 0.5 to about 5 weight percent from the circulating loop;
- (e) recovering at least a portion of the acetone from the reacted stream; and
- (f) recycling at least a portion of the acetone recovered in step (e) to the circulating loop in step (b).

20. The process of claim 19 wherein the cumene oxidation product mixture comprises a cumene hydroperoxide concentration from about 60 to about 95 weight percent.

21. The process of claim 19 wherein the ratio of the flow rate of cumene oxidation product mixture to the flow rate of the circulating loop is from about 1:10 to about 1:100.

22. The process of claim 19 wherein the acid catalyst is sulfuric acid.

23. The process of claim 19 wherein step (c) is conducted with one or more indirect heat-exchangers.

24. The process of claim 19 wherein the indirect heat-exchangers are essentially vertical.

25. The process of claim 19 wherein the weight ratio of the acetone recycle to the cumene oxidation product mixture is in the range from about 0.1:1 to about 2:1.

* * * * *